(12) United States Patent
Halliday

(10) Patent No.: US 8,083,676 B2
(45) Date of Patent: Dec. 27, 2011

(54) APPARATUS AND SYSTEM FOR COLLECTION AND STORAGE OF VITAL SIGNS MEDICAL INFORMATION AND METHODS RELATED THERETO

(76) Inventor: Thomas S. Halliday, Needham, MA (US)

(*) Notice: Subject to any disclaimer, the term of this patent is extended or adjusted under 35 U.S.C. 154(b) by 282 days.

(21) Appl. No.: 11/323,898

(22) Filed: Dec. 31, 2005

(65) Prior Publication Data

US 2007/0010724 A1   Jan. 11, 2007

(51) Int. Cl.
*A61B 5/00* (2006.01)
(52) U.S. Cl. ........ 600/301; 177/126; 600/485; 600/500; 600/549; 600/573
(58) Field of Classification Search .................. 600/301, 600/587; 177/25.12
See application file for complete search history.

(56) References Cited

U.S. PATENT DOCUMENTS

| | | | | |
|---|---|---|---|---|
| 3,508,653 A * | 4/1970 | Coleman | ...................... | 210/789 |
| 6,403,897 B1 * | 6/2002 | Bluth et al. | ................... | 177/144 |
| 6,428,124 B1 * | 8/2002 | Bluth et al. | ................... | 312/194 |
| 6,692,436 B1 * | 2/2004 | Bluth et al. | ................... | 600/300 |
| 2003/0042772 A1 * | 3/2003 | Park | ........................... | 297/217.1 |
| 2004/0069541 A1 * | 4/2004 | Perry | ............................. | 177/126 |
| 2004/0260156 A1 * | 12/2004 | David et al. | ................... | 600/300 |
| 2005/0052066 A1 * | 3/2005 | Wright | ..................... | 297/411.36 |

* cited by examiner

*Primary Examiner* — Max Hindenburg
*Assistant Examiner* — Michael C Stout
(74) *Attorney, Agent, or Firm* — Edwards Wildman Palmer LLP; Peter F. Corless; William J. Daley, Jr.

(57) ABSTRACT

Featured is an apparatus for the collection and storage of patient vital sign information as well as systems and methods related thereto. Such a collection and storage apparatus of the present invention forms a workstation that is configured and arranged so as to be capable of acquiring one or more pieces of patient vital sign information and/or data. Such an apparatus includes a re-configurable chair that can adapted to support one or more diagnostic devices, such as a scales and one or more vital sign monitors that are configured and arranged with circuitry and devices to measure and/or monitor any one or more of blood pressure, pulse $O_2$ saturation, body temperature, or blood sugar.

16 Claims, 4 Drawing Sheets

1 …
APPARATUS AND SYSTEM FOR COLLECTION AND STORAGE OF VITAL SIGNS MEDICAL INFORMATION AND METHODS RELATED THERETO

FIELD OF INVENTION

The present invention generally relates to apparatuses, devices, systems and methods for the collection and storage of patient vital sign medical data/information and more particularly to a an apparatus that is configured so as to be capable of collecting patient vital sign medical information/data using a single work station without the need for inputting of such information by medical personnel.

BACKGROUND OF THE INVENTION

When a patient arrives at a physician's office, a clinic, an out patient clinic, hospital admissions (e.g., day surgery) or an emergency room, it is standard practice to acquire vital signs data/information representative of the patient's general condition as well as data/information that is used for diagnosis and treatment of the patient. Such vital sign information for a patient includes for example, weight, blood pressure, pulse, $O_2$ saturation, body temperature, and blood sugar/glucose level. In practice, the collection process to acquire such vital sign information particularly in outpatient or physician settings generally involves the use of multiple diagnostic devices to obtain the desired measurements. In addition, it is the usual and customary practice for the measurements or acquired patient vital sign information/data to be manually recorded by the medical personnel and also manual inputting of the information into a patient information database.

The trend of physician practice, particularly in light of recent regulatory changes with regards to the control of the disclosure of patient information including vital sign information, is to promote obtaining such information while maintaining confidentially of the measurements/acquired information. While this practice is being promoted, the typical exam room setting (e.g., in a physician's office), however, is not configured and arranged (e.g., sized) so as to be capable of hosting all of the multiple diagnostic devices.

Consequently and as illustrated in FIG. 1, the present practice is to locate all the different multiple diagnostic devices in a centralized location. This practice can, however, create an environment whereby acquired information could be inadvertent or accidentally disclosed to third parties. In addition, because the centralized location is not the exam room this practice can involve additional walking or movement by the patient which can be problematic particularly when dealing with elderly patients. Also, because these are centralized areas, patients may not be ideally dressed for the particular data or information to be acquired. For example, a patient may be fully clothed so the measured weight includes the weight of clothing and shoes or the blood pressure reading may be affected by the clothing being worn by the patient.

Another practice in use, is to disperse the diagnostic devices such as for example, localizing the scale for weighting the patient in an alcove off or in a hallway, moving other devices about the facility to different exam rooms and/or having the patient go to a dedicated laboratory or testing facility for the acquisition of vital sign data. This practice has the shortcomings as indicated above of requiring the patient to move about the facility or having the medical personnel move the different medical instrumentalities/devices about the facility.

In these cases, it also would be necessary for the medical personnel after they acquired the vital sign information to manually record the vita sign information and also to input this information into a medical database. Such recording and inputting is subject to errors due to incorrect recordal or entry of measurements or incorrect recordal or entry of identifying information (e.g., incorrect entry of barcode) of patient samples that are to be tested and/or used for culturing for diagnostic purposes. Consequently, the increase adoption of electronic medical recording keeping necessarily involves a medical assistant or user to collect and verify all patient vital sign measurement data for submission as collected data to the patient's medical record.

It thus would be desirable to provide a new device, apparatus, system for the collection and storage of vital sign measurements/data and methods for such collection and storage. It would be particularly desirable to provide such a device, apparatus, system and method whereby all diagnostic measuring devices can be arranged so as to be located in an exam room and which would be easily operated by the medical personnel/assistant/user. It also would be particularly desirable to provide such a device, apparatus, system and method whereby the data can be collected, stored locally and associated with a given patient/patient record. The acquired information for the patient also preferably is transmitted or communicated to the facility electronic medical record keeping systems and/or communicated/transmitted to a physician (e.g., an attending physician or physician consultant) that is remote from the facility. It also would be particularly desirable to provide such a device, apparatus, system and method whereby the workflow of the medical personnel for the acquisition of such patient vital sign information/data is streamlined and the time needed for the acquisition of such information/data is reduced in comparison to the time required to acquire data using prior art devices/techniques and thereby also reduce patient encounter time. Such devices, apparatuses and systems preferably would be simple in construction and less costly than prior art devices and such methods would not require highly skilled users to utilize the apparatus.

SUMMARY OF THE INVENTION

The present invention features an apparatus for the collection and storage of patient vital sign information as well as systems and methods related thereto. In its broadest aspects, such a collection and storage apparatus of the present invention forms a workstation that is configured and arranged so as to be capable of acquiring one or more pieces of patient vital sign information and/or data. Such an apparatus also can be advantageously sized, configured and arranged so as to be generally capable of being located in a room such as an exam room.

Such an apparatus includes a re-configurable chair that can adapted to support one or more diagnostic devices, such as a scale and one or more vital sign monitors that are configured and arranged with circuitry and devices to measure and/or monitor any one or more of blood pressure, pulse, $O_2$ saturation, body temperature, or blood sugar. In particular embodiments, the chair includes a frame that has a structure configured to support the weight of a patient and to removably support the scale and the one or monitors as well as other related electronic and/or computing devices.

The chair also is configured to include a seat element on which the patient can sit. The seat element and the frame are each configured and arranged so that the seat can be re-positioned or moved between a seated position and a position for acquiring weight information. In particular embodiments, the seat element and the frame are configured and arranged so that the seat element is pivotably or rotatably mounted to the frame so that the seat element can be pivoted to a position to allow the weight data to be acquired (e.g., pivoted upwardly towards the back of the chair or pivoted upwardly towards the side of the chair).

The frame of the chair is further configured and arranged so as to support and position the scale for measuring the weight of the patient, such that when the seat element is repositioned into the position for acquiring weight information (e.g., pivoted upwardly towards the back of the chair) the scale is thereby exposed and sufficient room is provided so that the patient can step up onto the scale. In particular embodiments, the structure of the frame is further configured and arranged so as to provide one or more vertical extending sides or structures which provide a support mechanism for the patient in the case the patient becomes unsteady on their feet so as to minimize the risk of the patient falling while on the scale.

The frame also is further configured and arranged so that the scale is removably supported and/secured thereto. In this way, if the scale becomes inoperable and needs to be replaced with an operable scale or the scale is being replaced according to a particular program (e.g., a scale testing and certification program), such removing and replacing of the scale can be easily accomplished where the apparatus/chair is located instead of having to remove and replace the apparatus/chair.

In further aspects of the present invention, the frame of the chair is configured and arranged so as to provided one or more vertically extending structures/side elements for the chair where at least one of the one or more vertically extending sides is arranged so as to provided a support surface for an arm or the like of a patient when they are seated in the chair. Such a support surface can be used for any of a number of tasks including but not limited supporting the arm for blood drawing or supporting the arm that is being coupled to an IV drip such as the IV drip coupled to a patient during stress testing.

In more particular embodiments, the structure of the frame forming the one or more vertically extending sides is configured and includes a mechanism so as to allow the vertically extending side to be adjusted and secured in any of a number of distances above the top surface of the seat element. In this way, the top surface of the one or more vertically extending sides can be arranged at an optimal height to suit the particular procedure being performed. In more specific embodiments, the top surface of the one or more vertically extending sides includes a mechanism for resiliently supporting the arm or extremity of the patient.

In further aspects of the present invention, the frame of the chair is configured and arranged so as to provide one or more structures, including one or more support elements, that support each of the one or more diagnostic devices such as the medical monitors for measuring vital sign information other than the weight of the patient. In more particular embodiments, the scale includes a remote display/monitor for displaying the weight of the patient. As such, the frame of the chair is further configured and arranged so the support structure, including one or more support elements, also supports the remote monitor/display for the scale. In a yet a more specific embodiment, the support structure is a pole that is mounted and or secured to the frame using any of a number of techniques known to those skilled in the art (e.g., welding, brazing, or mechanically such as by nuts and bolts) and one or more pole mounts that are securable to the pole and also provides a mechanism for securing the monitor to the pole mount.

Such support structures are preferably configured and arranged so that the diagnostic monitors and/or the scale's remote display/monitor are located at a convenient height above the floor so as to be easily viewed and observed by the medical personnel during use. In yet further embodiments, the frame and these support structures are arranged so that the support structures are generally located externally to the vertically extending sides of the chair so that the patient should not contact the support structure or the monitors mounted thereto when the patient is standing on the scale or when seated in the chair.

In yet further aspects of the present invention, each of the monitors are operably coupled to a computing device containing programs for execution therein. Such operably coupling can embody any of a number of communication techniques known to those skilled in the art, including wired communication techniques, optical communication techniques or wireless (e.g., IR or RF) communication techniques. Such a computer or computing device also includes an interface so as to be operably coupled to each of the one or more diagnostic devices/monitors and/or scale. Such an interface also is configurable so as to be capable of implementing the communication technique embodied in the above described operably coupling.

Such programs including instructions and criteria for controlling the acquisition of data/information from the scale and/or monitors secured to the chair and for the transmission of the acquired data in the appropriate format for entry into a electronic medical record system being used at the facility in which the chair is located. In further embodiments, the program includes instructions and criteria for interrogating the devices operably coupled thereto for purposes of validating and identifying acquired information so as to thereby minimize data acquisition errors.

Also featured are systems and methods related thereto.

Other aspects and embodiments of the invention are discussed below.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein.

DESCRIPTION OF THE PREFERRED EMBODIMENT

Figure 1:
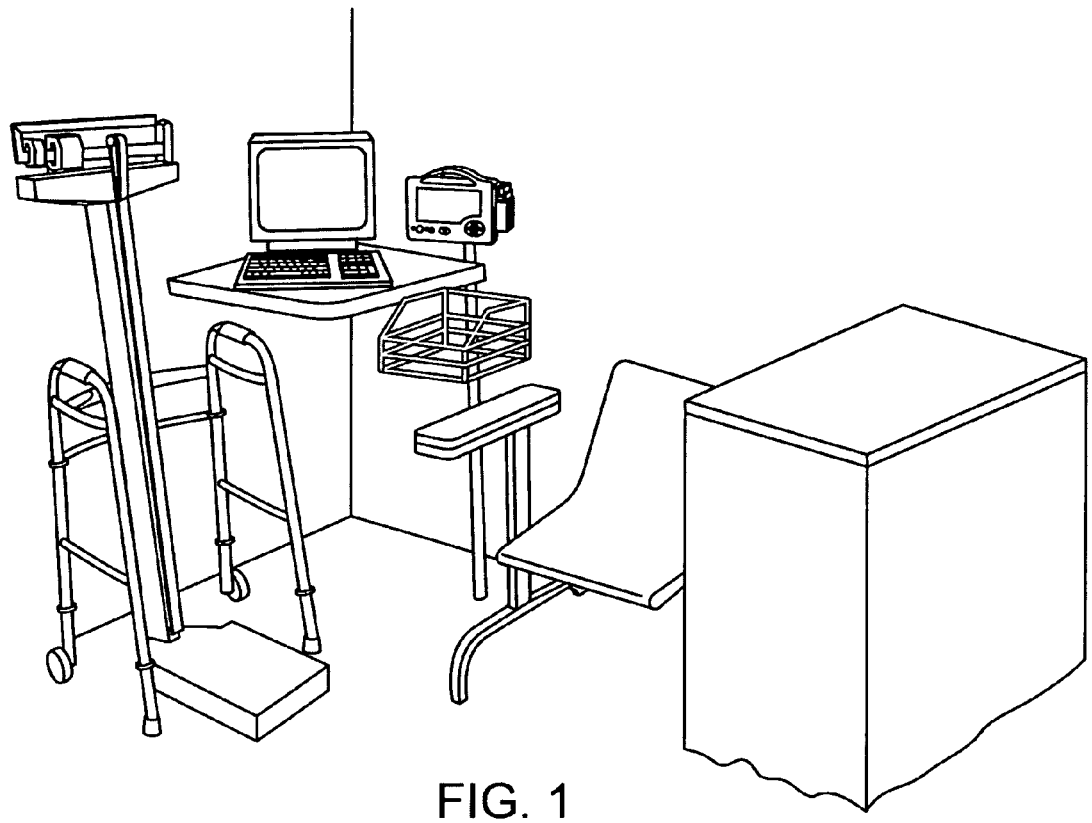
FIG. 1 is a perspective view of a conventional arrangement of medical/diagnostic devices that are located centrally.
Figure 3:
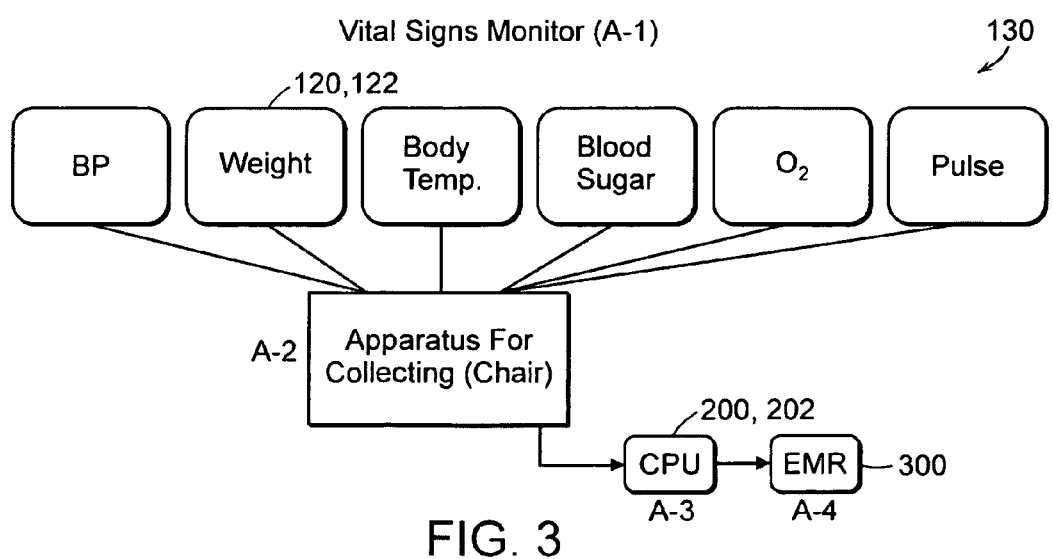
FIG. 3 is a block diagram schematically illustrating the arrangement of an collecting and storing apparatus of the present invention.
Figure 2A:
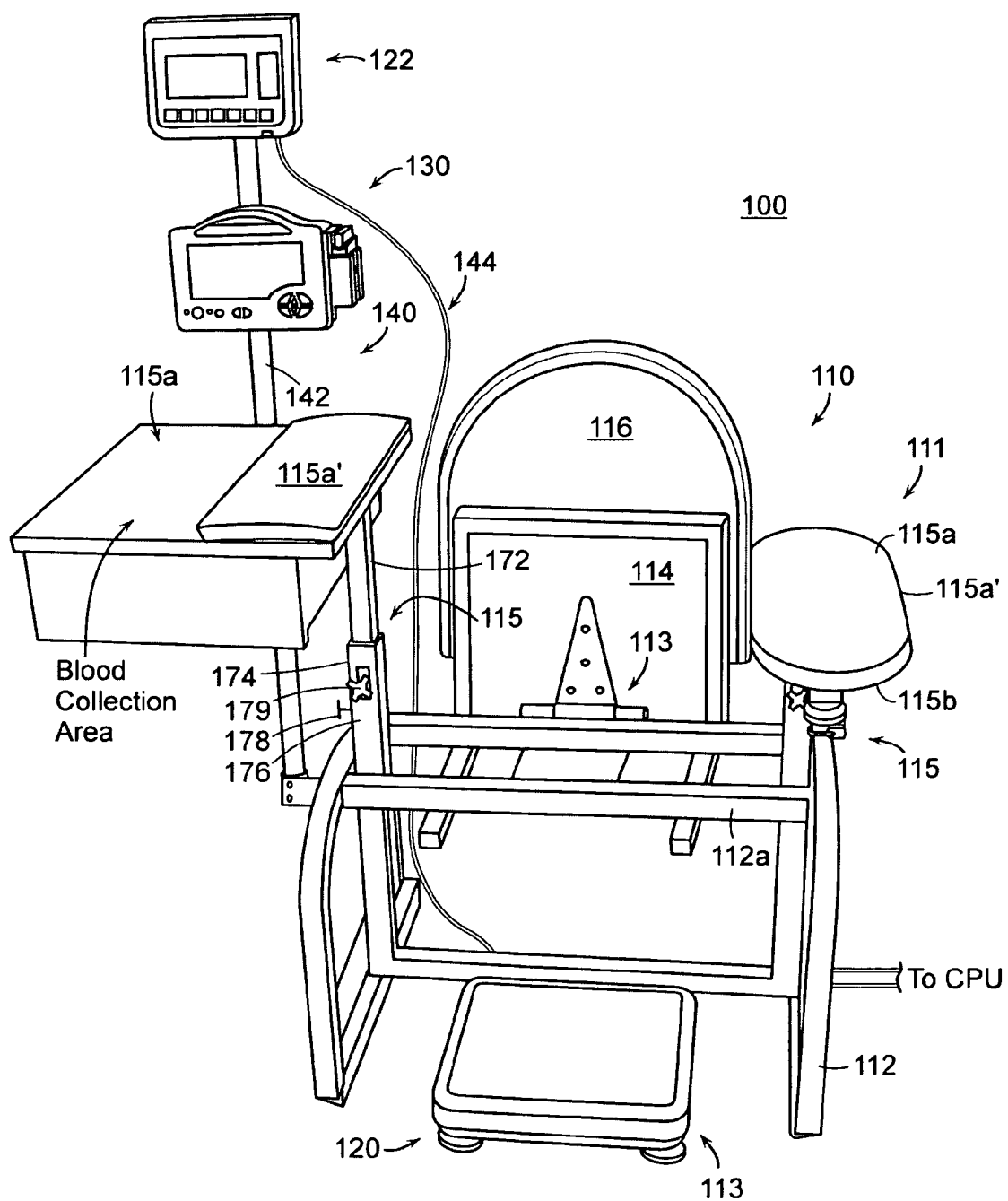
FIG. 2A is one perspective view of an apparatus or work station for collecting and storing vital sign information/data according to an aspect of the present invention with the seat positioned in the weight acquiring position.
Figure 2B:
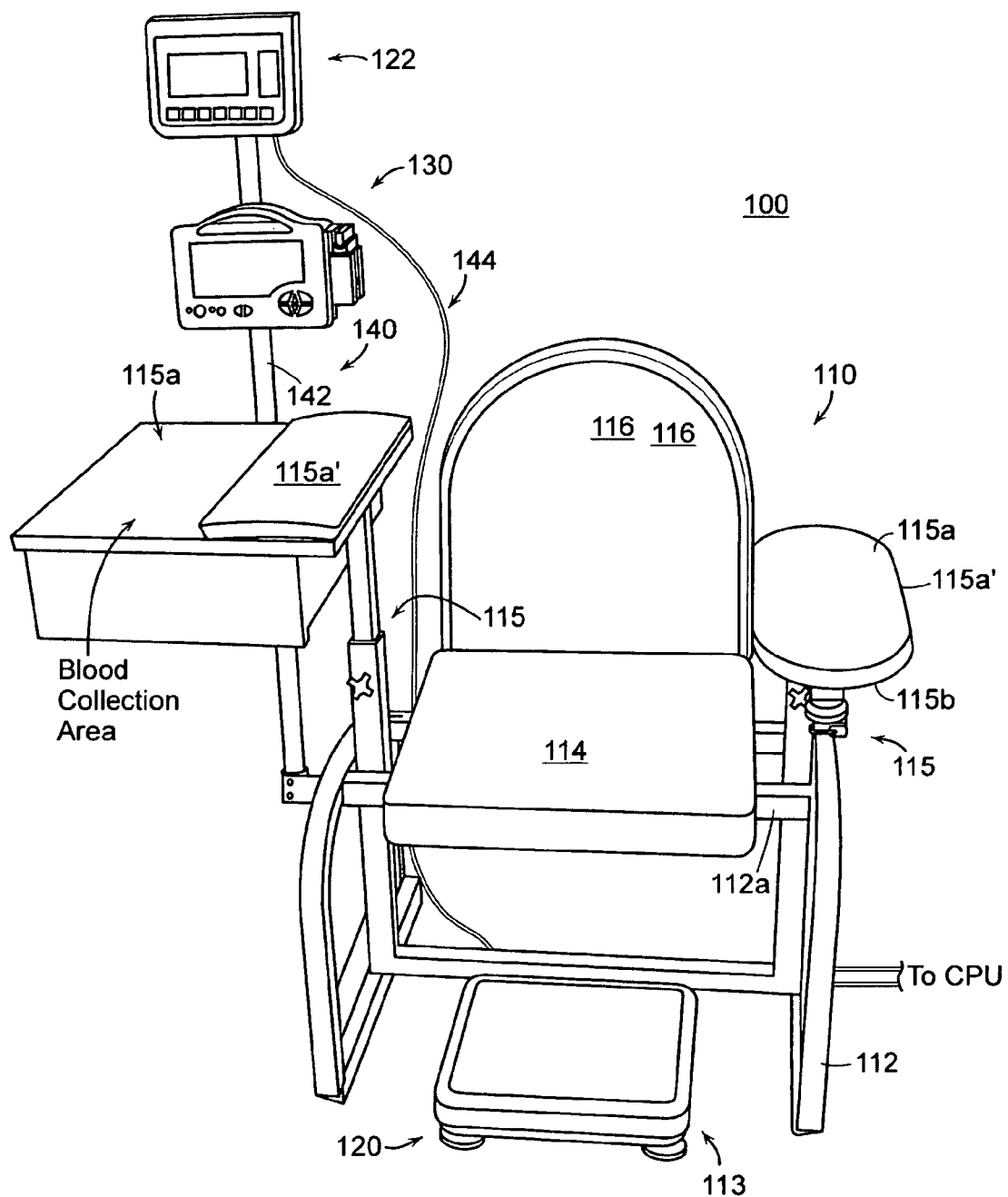
FIG. 2B is another perspective view of the apparatus or work station of FIG. 2A but with the chair seat positioned in the seated position.
Figure 2C:
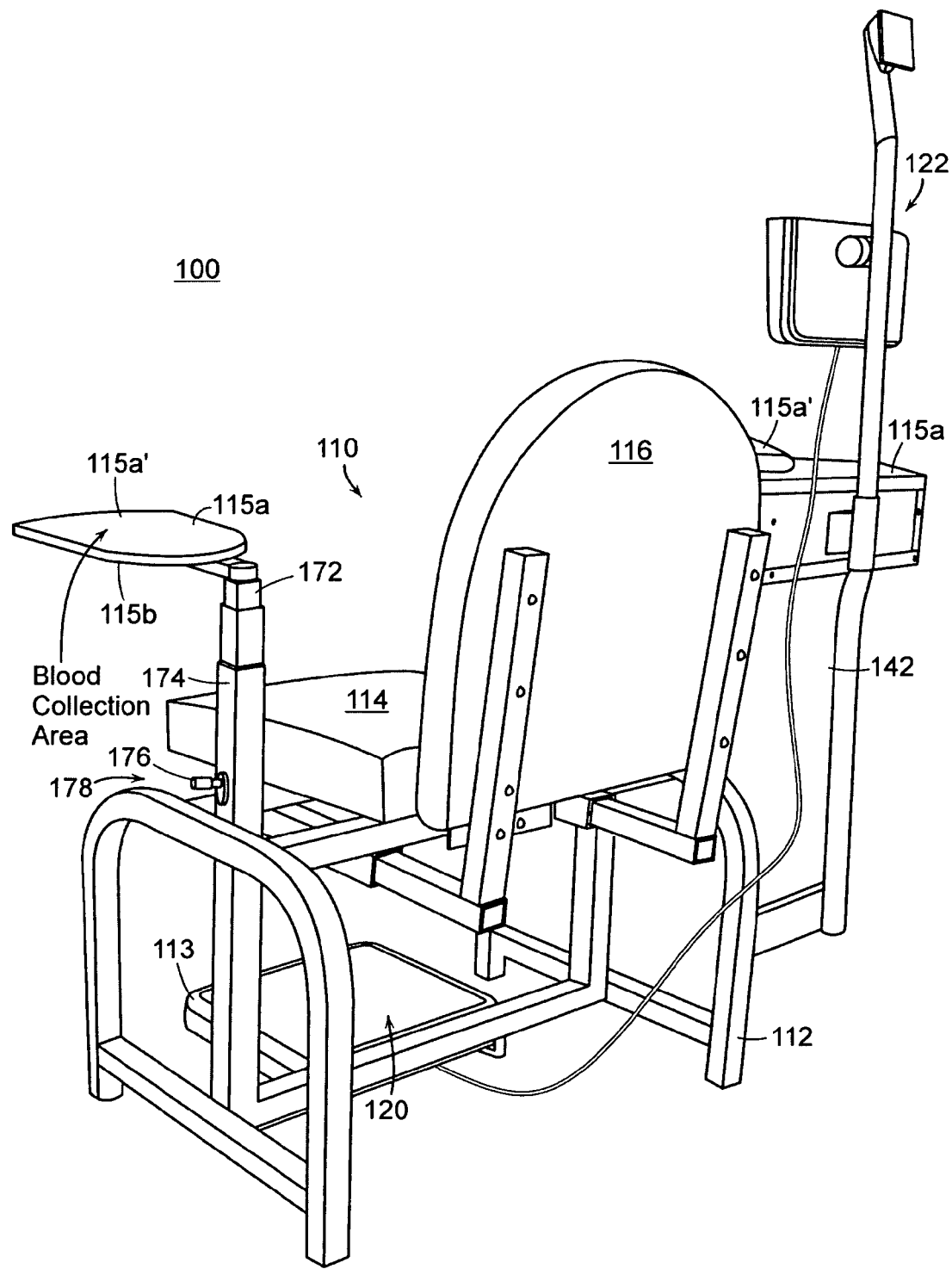
FIG. 2C is another perspective view of the apparatus or work station of FIG. 2A, but being a different perspective view from that shown in FIG. 2.

Referring now to the various figures of the drawing wherein like reference characters refer to like parts, there are shown in FIGS. 2A-C various perspective views of an apparatus 100 for the collection and storage of patient vital sign information/data according to the present invention and there is shown in FIG. 3 a block diagram view that schematically illustrates such an apparatus. A front perspective view of the apparatus 100 with the seat pivoted up and with the seated in the seated position are shown in FIGS. 2A and 2B, respectively and a rear perspective view is shown in FIG. 2C.

Such an apparatus 100 includes a chair 110, a scale 120 and one or more vital sign monitors 130 that can measure one or more vital sign information/data of a patient. In more specific embodiments, the apparatus 100 is arranged so that the chair 110, scale 120 and vital sign monitors 130 are arranged so as to in effect form a single vital sign work station with a built in chair and is capable of measuring any of a number of patient vital sign information/data including but not limited to one or more of weight, blood pressure, pulse, $O_2$ saturation, body temperature, or blood sugar.

In its broadest aspects, such an collection and storage apparatus 100 forms a workstation that is configured and arranged so as to be capable of acquiring one or more pieces of patient vital sign information and/or data. Such an apparatus 100 also is sized, configured and arranged so as to be generally capable of being located in a room such as an exam room of an existing facility (e.g., an exam room in the emergency admissions portion of a hospital) thereby minimizing the need to redesign facilities so as to be capable of using/hosting the apparatus.

The chair 110 includes a frame 112, a seat 114 and a back 116. The frame 112 has a structure that is formed and arranged using any of a number of techniques known to those skilled in the art to support the weight of a patient sitting on the seat 114 of the chair. In further aspects of the invention, and as described hereinafter, the frame 112 also is configured and arranged so as to form a support structure 113 for the scale 120 and for each of the one or monitors 130 as well as other related electronic and/or computing devices.

As indicated herein, the chair 110 is configured to include a seat 114 on which a patient can sit, such as when acquiring certain of the vital sign information. The seat 114 and the frame 112 also are each configured and arranged so that the seat can be re-positioned or moved between a seated position and a position for acquiring weight information. In particular embodiments, the frame 112 includes a pivot or hinge mechanism 113 that pivotably secures the seat 114 to the frame so that the seat 114 is pivotably or rotatably mounted to the frame. In this way, the medical personnel or patient can pivot the seat 114 to the weight data acquisition position such as for example, pivoting the seat upwardly and towards the back 116 of the chair or pivoting the seat upwardly and towards the side 111 of the chair. The frame 112 also is arranged so as to provide a crossing support member 112a that passes underneath the seat 114 so the seat rests on the crossing member when the seat is pivoted downwardly into the seating position.

The chair back 116 is secured to the frame and arranged so as to be at an appropriate angle with respect to the seat 114 for normal patient seating. It also is contemplated that the chair back 116 and the frame be configured so that the chair back can be positioned at any of a number of angles with respect to the seat 114. In this way, for example, the chair back 116 can be tilted backwards with respect to the seat 114 so the patient is in a reclined or semi-reclined position. It also is contemplated that the chair back 116 can be moved with respect to an end surface of the seat 114 (i.e., so the chair back is moved closer or further from the seat end surface). As is known to those skilled in the art, the seat 114 and chair back 116 comprise a resilient material and cover material over a rigid member so the patient is seating and/or resting upon a pliant, resilient surface.

As indicated herein, the frame 112 also is further configured and arranged so as to provide a supporting structure 113 for the scale 120. The frame 112 including the scale supporting structure 113 also is configured so as to position the scale within the apparatus 100 such that when the seat 114 is in the position for acquiring weight information such as shown in FIG. 2A (e.g., pivoted upwardly towards the back of the chair), the scale is exposed. In addition, the frame 112 is configured so that there is sufficient room provided within the apparatus/chair 100,110 such that the patient can step up onto the scale so the weight of the patient can be measured.

The frame supporting structure 113 for the scale 120 is further configured and arranged so that the scale is removably supported and/secured thereto. In this way, if the scale 120 becomes inoperable and needs to be replaced with an operable scale or the scale is to be replaced according to a particular program (e.g., a scale testing and certification program), such removing and replacing the scale can be easily accomplished where the apparatus 100 is located instead of having to remove and replace the entire apparatus.

In particular embodiments, the frame 112 is configured and arranged so as to provide one or more structures 115 that each comprise one or more vertical extending sides 111 of the chair 110. These one or more vertically extending structures 115 or sides 111 provide a support mechanism for the patient in the case the patient becomes unsteady on their feet while standing upon the scale or when step up onto or stepping of the scale. This thereby minimizes the risk of the patient falling while on the scale or getting on or off the scale. Also, the patient can use such structures 115 for getting into and out of the chair, for example, the patient could push off against the structure(s) with their hands to provide assistance in getting out of the chair.

In further aspects of the present invention, at least one of the one or more vertically extending structures 115 or sides of the chair 110 also is arranged so as to provided a support surface 115a for the arm or like of a patient when they are seated in the chair. The support surface 115a also is arranged so that it generally extends horizontally and in a front to back direction of the chair. Such a support surface 115a can be used for any of a number of tasks including but not limited supporting the arm for blood drawing or supporting the arm that is being coupled to an IV drip such as the IV drip coupled to a patient during stress testing.

In more particular embodiments, the one or more vertically extending structures 115 forming the sides 111 of the chair 110 are configured so as to include a mechanism that allows the vertically extending structures 115 to be adjusted and secured in any of a number of vertical distances above the top surface of the seat 114. In this way, the support surface 115a of the one or more vertically extending structures 115 or sides can be arranged at an optimal height to suit the particular procedure being performed. In more specific embodiments, the one or more vertically extending structures 115 is configured to include a mechanism or member 115a' that resiliently supports the arm or extremity of the patient. In an exemplary embodiment, the resilient support member 115a' is a resilient pad that is secured to a horizontally extending support member 115b secured to the vertically extending structure 115. In this embodiment, the top surface of the resilient support member 115a' forms the support surface 115a.

The mechanism that allows the vertically extending structure 115 to be adjusted and secured a desired distance from the seat top surface embodies any of a number of techniques known to those skilled in the art and adaptable for use with the frame 112 of the chair 110. In an illustrated embodiment, the structure of the vertically extending structure is adapted so as to include a tube-within-a-tube type of structure, in which an inner member 172 is moveably disposed within an outer member 174. The outer member 174 also includes one or more threaded through holes 176 in which is threadably received a tightening member 178 having an enlarged end 179. In use, the user would secure the inner member 172 within the outer member 174 by rotating the tightening member enlarged end 179 until the opposite end of the tightening member contacts and stop the inner member from further axial movement. Correspondingly, the user would loosen the tightening member to allow the inner member to be moved thereby allowing the vertically extending side to be adjusted to a desired position.

In further aspects of the present invention, the frame 112 of the chair 110 is configured and arranged so as to provide one or more support structures, including one or more support elements, that support each of the one or more diagnostic devices such as the medical or diagnostic monitors 130 that measure vital sign information other than the weight of the patient. In more particular embodiments, the scale 120 includes a remote display/monitor 122 that displays the weight of the patient. As such, the frame 112 of the chair 110 also is configured and arranged so as to provide a structure, including one or more support elements, that supports the scale's remote monitor/display 122.

In more specific embodiments, a support structure 140 including a plurality or more of support elements is provided that supports each of the one or more diagnostic devices 130 and the scale's remote monitor/display 122. In yet a more specific embodiment, the support structure 140 is a pole 142 and one or more pole mounts 144 that are securable to the pole and also provide a mechanism for securing the monitor 122, 130 to the pole mount. The pole 142 also is mounted and/or secured to the frame 112 using any of a number of techniques known to those skilled in the art that is appropriate for the materials of the frame and the support structure (e.g., welding, brazing, or mechanically such as by nuts and bolts). In more specific embodiments the pole mounts 144 are removably secured to the pole 142 and the monitors 122, 130 are removable secured to the pole mounts using any of a number of techniques known to those skilled in the art (e.g., bolts, wing nuts, etc.).

Such a support structure 140 is preferably configured and arranged so that the diagnostic monitors 130 and/or the scale's remote display/monitor 122 are located at a convenient height above the floor so as to be easily viewed and observed by the medical personnel during use. In yet further embodiments, the frame 112 and the support structure 140 are arranged so that the support structure 140 is generally located externally to the vertically extending structures 115 comprising the sides of the chair 110 so that the patient should not contact the support structure 140 nor the monitors 122, 130 mounted thereto when the patient is standing on the scale 120 or when the patient is seated in the chair.

In yet further aspects of the present invention, each of the monitors 122, 130 are operably coupled to a computing device or computer 200 that includes programs for execution on a CPU 202 therein. Such programs including instructions and criteria for controlling the acquisition of data/information from the scale and/or monitors of the apparatus 100 and for the transmission of the acquired data in the appropriate format for entry into an electronic medical record system 300 being used at the facility in which the apparatus 100 is located. In further embodiments, the program includes instructions and criteria for interrogating the devices or monitors 122, 130 operably coupled thereto for purposes of validating and identifying acquired information so as to thereby minimize data acquisition errors. Such a computer 200 also includes an interface so as to operably couple each of the one or more diagnostic devices/monitors 122, 130 and/or scale 120 thereto.

The process of acquiring, collecting and storing vital sign data/information as well the methodology and functionalities of the software program being executed on the computer CPU 202 can be best understood from the following discussion along with reference to FIGS. 2-3 and the discussion thereto. Although the following discussion describes the methodology and other related aspects of the present invention in terms of acquiring more than one piece of vital sign data/information, it should be recognized that it is contemplated and thus within the scope of the present invention for one piece of vital sign data such as patient weight be acquired using the apparatus 100 of the present invention as well as the apparatus being configured so to only be capable of acquiring this one piece of vital sign data.

The apparatus 100 according to the present invention is arranged so that one or more monitoring devices 122, 130 and the scale are mounted to the frame 112 of the chair 110. Further it is contemplated that each of the monitors 122, 130 are operably coupled to the computer 200 using any of a number of communication techniques known to those skilled in the art (e.g., wired, wireless, optical). In more particular embodiments, the computer 200 is operably coupled to the electronic medical record system of the facility using any of a number of techniques known to those skilled in the art including via local or wide area communication networks.

The computer 200 is loaded with a software component or program, which includes instructions and criteria to associate collected vital sign measurement data with a selected patient's medical record. The software also includes instructions and criteria so that the computer 200 is able to submit collected vital sign data into the selected patient's electronic medical record. In further embodiments, the software program includes instructions and criteria so as to allow the computer to interface with a patient census/scheduling system to collect a list of patients.

Using the apparatus 100 of the present invention, the seat 114 of the chair is lifted up to expose the scale or weighing device, the patient steps up onto the scale and the weight of the patient is measured. Because the patient is likely not to be fully clothed but rather clothed for purposes of the examination, the weight being measured is more closely to the actual weight of the patient. The measured weight is preferably communicated to the computer 200 via the operable connection between the scale monitor 122 and the computer. In this way, transcription and/or inputting errors that may occur using conventional techniques are thereby minimized if not avoided.

Thereafter, the patent would step off the scale 120, the seat pivoted back to the seated position and the patient would then be asked to sit down in the chair. Thereafter, the medical personnel would attach the appropriate leads/devices so as to allow other vital sign information/data to be acquired. For example, a device would be attached to the patient's fingertip that allows for measurement of pulse and blood $O_2$ saturation and/or a cuff attached about the patient's arm to measure blood pressure.

In addition, the medical personnel also could draw blood from the patient using known techniques where the patient's arm from which the blood would be drawn, is supported on the support surface 115a of one of the one or more vertically extending structures 115. The blood samples can be coded into the computer 200 using the work station interface provided by the apparatus 100. In addition, the software program being executed further includes instructions and criteria for interrogating the applicable device/monitor 130 of the particular apparatus and to verify that the blood sample(s) were not coded incorrectly. Thus, thereby minimizing errors that could lead to tracking blood samples and/or relating the blood sample analysis results to the patient.

In more particular embodiments, one of the monitors 130 is any one of a number of devices or glucose meters known in the art that are configured and arranged so as to be capable of measuring blood sugar or glucose levels and for providing an output of the measured result.

In contrast to the present invention, the current process for collecting vital sign information includes; measuring patient weight at a weight station; measuring blood pressure, pulse, temperature in the exam room, and drawing a blood sample and measuring glucose/blood sugar at a separate drawing station. Because of the single workstation arrangement embodied in the present invention, one can measure patient weight, blood pressure, pulse, $O_2$ Saturation, temperature at a single vital sign station as well as measuring patient glucose in the same vital sign station and/or drawing blood at the single vital station. This improves the process and workflow of the medical personnel and necessarily reduces the patient encounter time.

Although a preferred embodiment of the invention has been described using specific terms, such description is for illustrative purposes only, and it is to be understood that changes and variations may be made without departing from the spirit or scope of the following claims.

INCORPORATION BY REFERENCE

All patents, published patent applications and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A method for acquiring vital sign information, comprising the steps of:
    providing a chair having
        a frame and a seat element movably coupled to the frame, that is moveable between a seated position and a weight data acquisition position,
        a scale positioned with respect to the frame such that when the seat is moved so as to be in the weight data acquisition position, the scale is exposed and a sufficient area is provided within the frame so that a patient can step up onto the scale and when the seat is in the seated position weight data of the patient is not acquied by action of a patient sitting on the seat,
        a storage device for receiving a weight measurement,
        the frame being configured so as to include one or more adjustable vertically extending structures that form sides of the chair, the one or more adjustable vertically extending structures being arranged so as to form a support surface for an arm of a patient when the patient is seated on the seat, the one or more adjustable vertically extending structures including an adjustment mechanism so that the support surface can be adjusted to any of a number of vertical distances with respect to the seat, and
        a monitoring device operable coupled to the scale for one of displaying the measured weight or communicating the measurement to the storage device; and
    raising the seat so as to expose the scale;
    standing on the scale by a patient when the seat is raised; and
    measuring the weight of the patient when the seat is raised.

2. The method of claim 1, further comprising the step(s) of:
    measuring at least one of blood pressure, pulse, or temperature.

3. An apparatus for collecting and storing vital sign data, comprising:
    a chair having a frame and a seat element movable coupled to the frame that is moveable between a seated position and a weight data acquisition position;
    a scale positioned with respect to the frame such that when the seat is moved so as to be in the weight data acquisition position, the scale is exposed and a sufficient area is provided within the frame apparatus so that a patient can step up onto the scale and when the seat is in the seated position weight data of the patient is not acquired by action of a patient sitting on the seat,
    a storage device for receiving a weight measurement,
    the frame being configured so as to include one or more adjustable vertically extending structures that form sides of the chair, the one or more adjustable vertically extending structures being arranged so as to form a support surface for an arm of a patient when the patient is seated on the seat, the one or more adjustable vertically extending structures including an adjustment mechanism so that the support surface can be adjusted to any of a number of vertical distances with respect to the seat, and
    a monitoring device operable coupled to the scale for one of displaying the measured weight or communicating the measurement to the storage device.

4. The method of claim 1, wherein the one or more adjustable vertically extending structures being arranged so as to form a support surface for an arm of a patient is configured and arranged so as to form a blood collection station, and wherein said method further includes the steps of:
    drawing blood from the patient; and
    measuring glucose or blood sugar level using the drawn blood.

5. An apparatus for collecting and storing vital sign data, comprising:
    a chair having a frame and a seat element movable connected to the frame so as to moveable between a seated position and a weight data acquisition position,
    a scale positioned with respect to the chair frame such that when the seat is moved so as to be in the weight data acquisition position, the scale is exposed and a sufficient area is provided within the frame so that a patient can step up onto the scale to be weighed and when the seat is in the seated position weight data of the patient is not acquired by action of a patient sitting on the seat,
    a storage device for receiving a weight measurement,
    a monitoring device operable coupled to the scale for one of displaying the measured weight or communicating the measurement to the storage device,
    a support structure including a plurality of support elements that are arranged to support the monitoring device, wherein the plurality of support elements is secured to the chair frame such that the support structure is external to the frame of the chair so that the patient does not contact the support structure or the monitoring device when standing on the scale or seated on the seat.

6. The apparatus of claim 5, further comprising one or more additional monitoring devices each being supported by the support structure, the one or more additional monitoring devices being configured to measure any one or more vital sign information/data and for one of displaying the measured measurement or communicating the measurement to the storage device, wherein the vital sign information data being measured by the one or more additional monitoring devices includes one or more of blood pressure, pulse, $O_2$ Saturation, or body temperature.

7. The method of claim 1, wherein the chair being provided further includes one or more additional monitoring devices configured to measure any one or more vital sign information or data and for one of displaying the measured measurement or communicating the measurement to the storage device, and wherein the method further comprises the steps of:
seating a patient in the chair;
coupling the patient to the one or more device; and
acquiring the vital sign information.

8. The method of claim 7, further comprising the steps of:
providing a computing device including an applications program for execution therein;
operably coupling each of the one or more monitoring devices to the computing device;
communicating the acquired vital sign information from the one or more monitors to the computing device.

9. The method of claims 1, further comprising the steps of:
providing a computing device including an applications program for execution therein;
operably coupling the scale to the computing device;
communicating the acquired weight information to the computing device.

10. The method of claim 9, further comprising the steps of:
operably coupling the computing device to a data store of patient records;
communicating the weight information communicated to the computing device to the data store.

11. The method of claim 8, further comprising the steps of:
operably coupling the computing device to a data store of patient records;
communicating the vital sign information communicated to the computing device to the data store.

12. The apparatus of claim 3, wherein the one or more adjustable vertically extending structures being arranged so as to form a support surface for an arm of a patient is configured and arranged so as to form a blood collection station.

13. The apparatus of claim 3, further comprising a device support structure including a plurality of support elements that are arranged to support the monitoring device, wherein the plurality of support elements is secured to the supporting structure of the chair frame such that the device support structure is external to the frame of the chair so that the patient does not contact the device support structure or the monitoring device when standing on the scale or seated on the seat.

14. The apparatus of claim 13, further comprising one or more additional monitoring devices each being supported by the device support structure, the one or more additional monitoring devices being configured to measure any one or more vital sign information or data and for one of displaying the measured measurement or communicating the measurement to the storage device, wherein the vital sign information or data being measured by the one or more additional monitoring devices includes one or more of blood pressure, pulse, $O_2$ Saturation, or body temperature.

15. The apparatus of claim 14, wherein the device support structure is configured and arranged so that a display of a given monitoring device is located a distance above the ground so as to be at a convenient height for viewing by a clinician.

16. The apparatus of claim 5, wherein the device support structure is configured and arranged so that a display of a given monitoring device is located a distance above the ground so as to be at a convenient height for viewing by a clinician.

* * * * *